(12) United States Patent
Yamaya

(10) Patent No.: US 9,993,145 B2
(45) Date of Patent: Jun. 12, 2018

(54) WASHING INSTRUMENT FOR INSERTION DEVICE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/456,806

(22) Filed: Mar. 13, 2017

(65) Prior Publication Data

US 2017/0181611 A1 Jun. 29, 2017

Related U.S. Application Data

(63) Continuation of application No. PCT/JP2015/075910, filed on Sep. 11, 2015.

(30) Foreign Application Priority Data

Oct. 15, 2014 (JP) ................................. 2014-210879

(51) Int. Cl.
*A61B 1/12* (2006.01)
*B08B 9/032* (2006.01)

(52) U.S. Cl.
CPC .............. *A61B 1/123* (2013.01); *A61B 1/125* (2013.01); *B08B 9/0321* (2013.01)

(58) Field of Classification Search
None
See application file for complete search history.

(56) References Cited

U.S. PATENT DOCUMENTS 7,475,697 B2 * 1/2009 Sasaki ................... A61B 90/70
134/166 C
2009/0205687 A1 * 8/2009 Onishi ................... B08B 9/032
134/136

FOREIGN PATENT DOCUMENTS

JP H08-196505 A 8/1996
JP 2012-045327 A 3/2012
(Continued)

OTHER PUBLICATIONS

English translation of International Preliminary Report on Patentability dated Apr. 27, 2017 together with the Written Opinion received in related International Application No. PCT/JP2015/075910.
(Continued)

*Primary Examiner* — Michael E Barr
*Assistant Examiner* — Cristi J Tate-Sims
(74) *Attorney, Agent, or Firm* — Scully, Scott, Murphy & Presser, P.C.

(57) ABSTRACT

A washing instrument for an insertion device performs positioning of a distal portion by an axial direction regulating portion provided in a cylindrical hollow washing instrument main body and abutting on the distal portion of the insertion device, and a rotating direction regulating portion facing an observation surface of the insertion device, thereby attaching the insertion device. A raised distal portion of a swing base received in a receiving chamber of the distal portion abuts on a projecting locking portion provided on an inner peripheral surface between the washing ports, the locking portion and the axial direction regulating portion hold a positioned state of the distal portion, and washing liquids jetting out from the washing ports directly collide with washing target regions of the receiving chamber to perform washing.

13 Claims, 12 Drawing Sheets

(56) References Cited

FOREIGN PATENT DOCUMENTS

JP            2012045327 A  *  3/2012
WO    WO 2015/107801 A1      7/2015

OTHER PUBLICATIONS

International Search Report dated Dec. 8, 2015 issued in PCT/JP2015/075910.
Chinese Office Action dated Aug. 10, 2017 received in 201580027917.3.
Chinese Office Action dated Mar. 20, 2018 received in Chinese Patent Application No. 201580027917.3, together with an English-language translation.

* cited by examiner

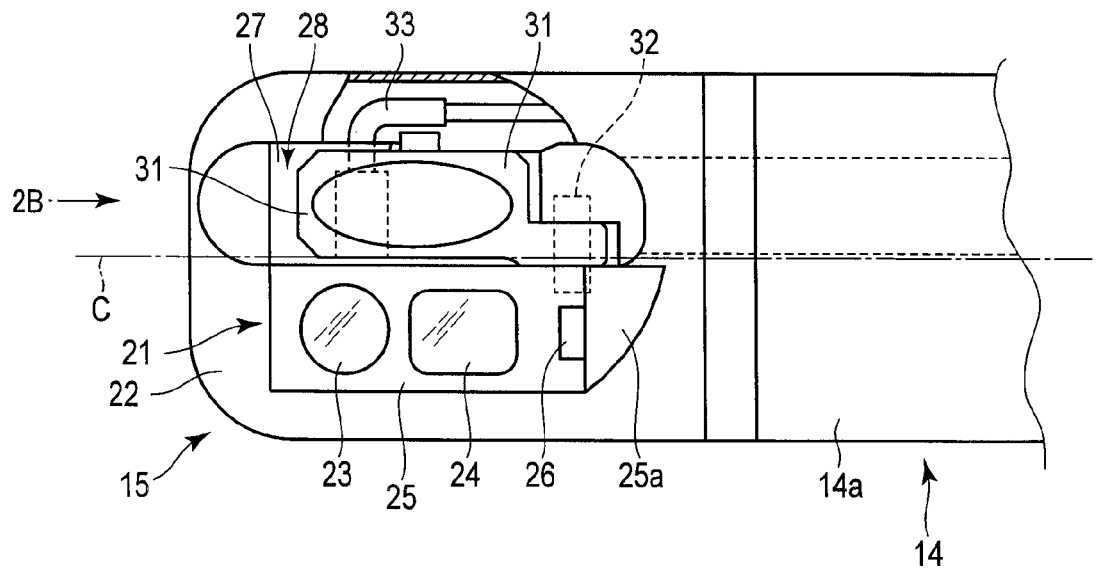
F I G. 2A
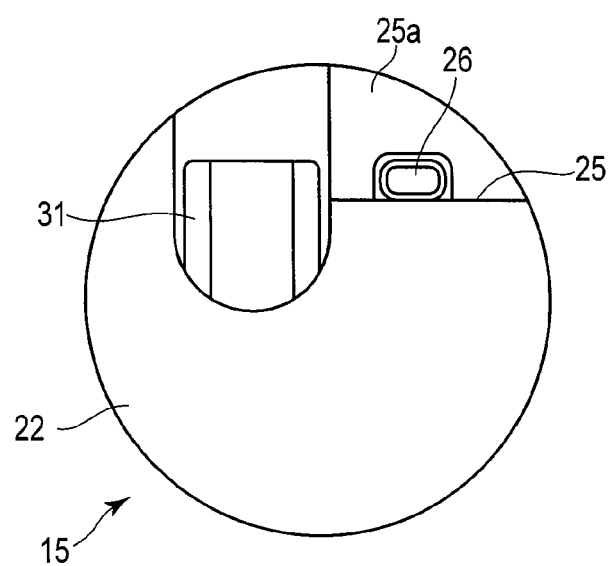
F I G. 2B

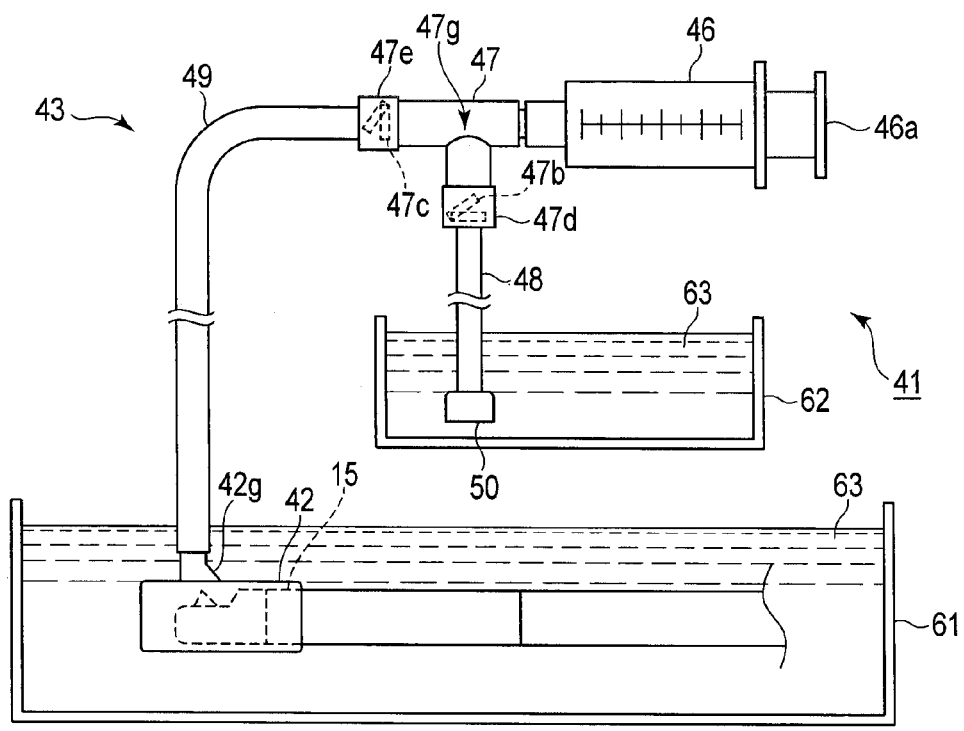
F I G. 4B
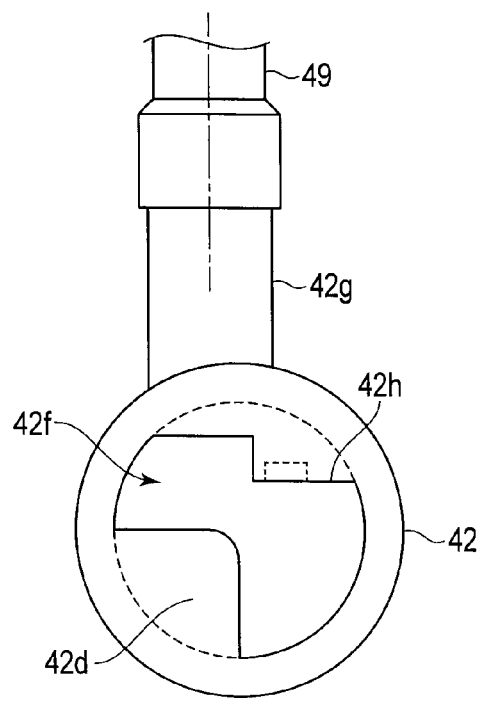
F I G. 5

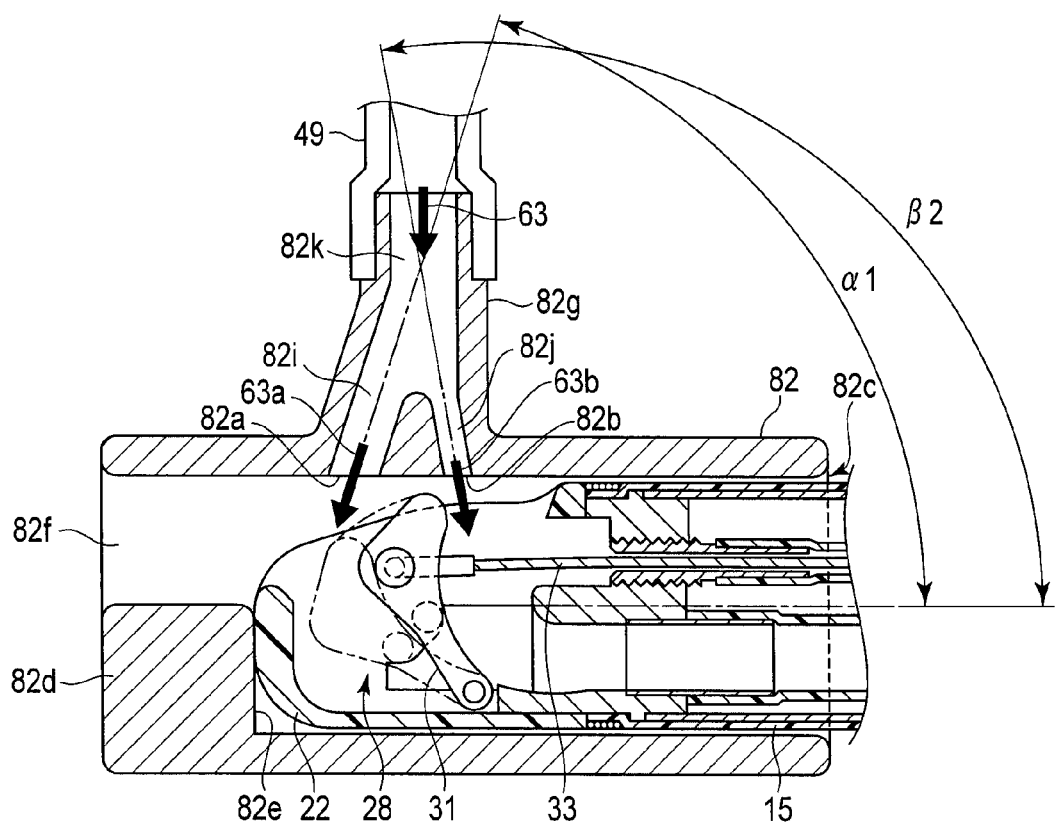
F I G. 10

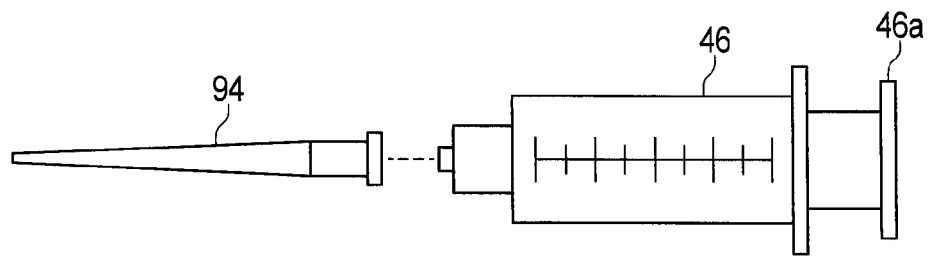
F I G. 12
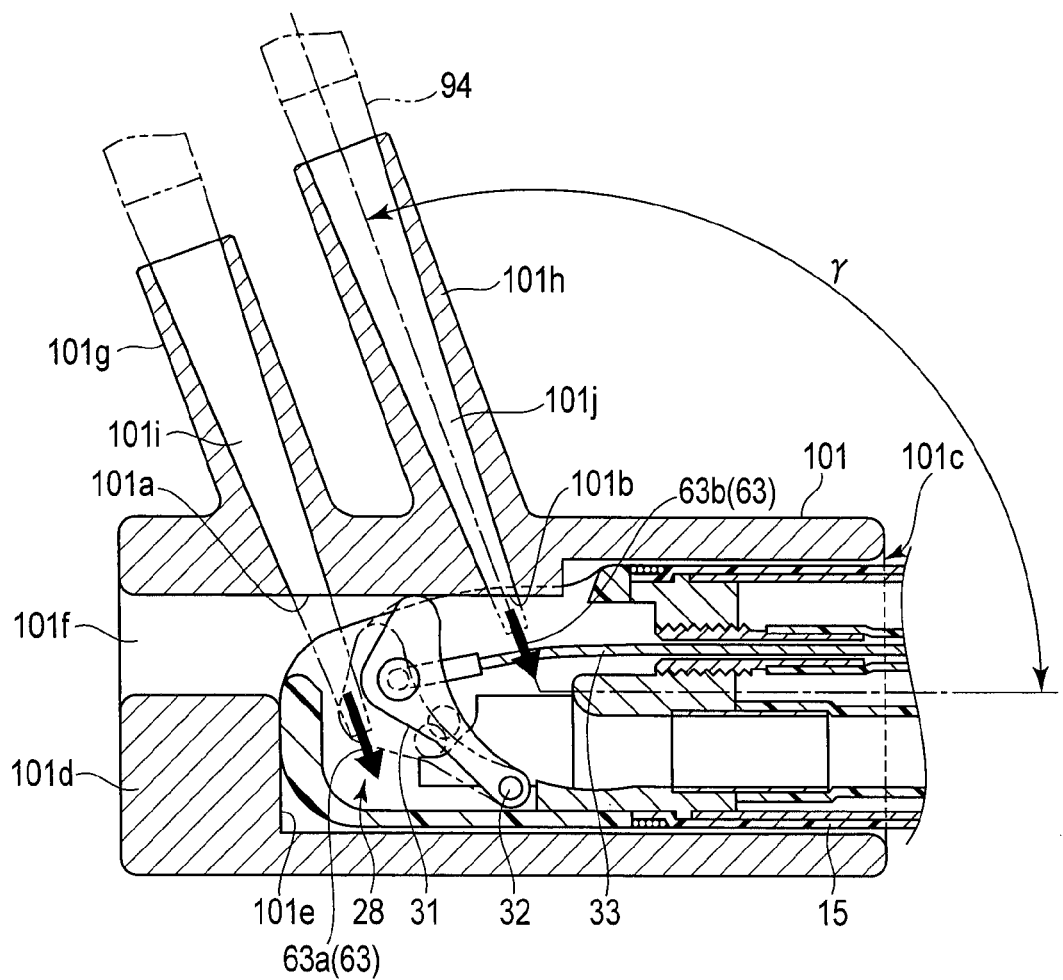
F I G. 13A

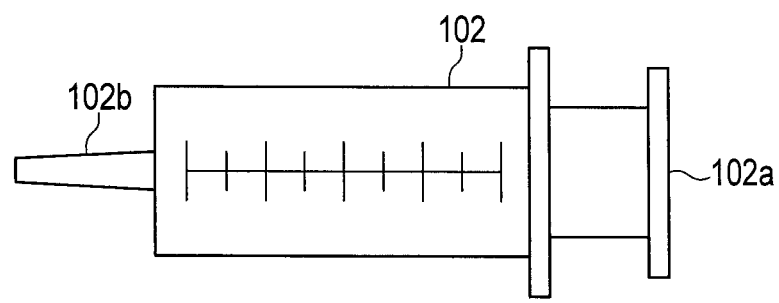
F I G. 15A
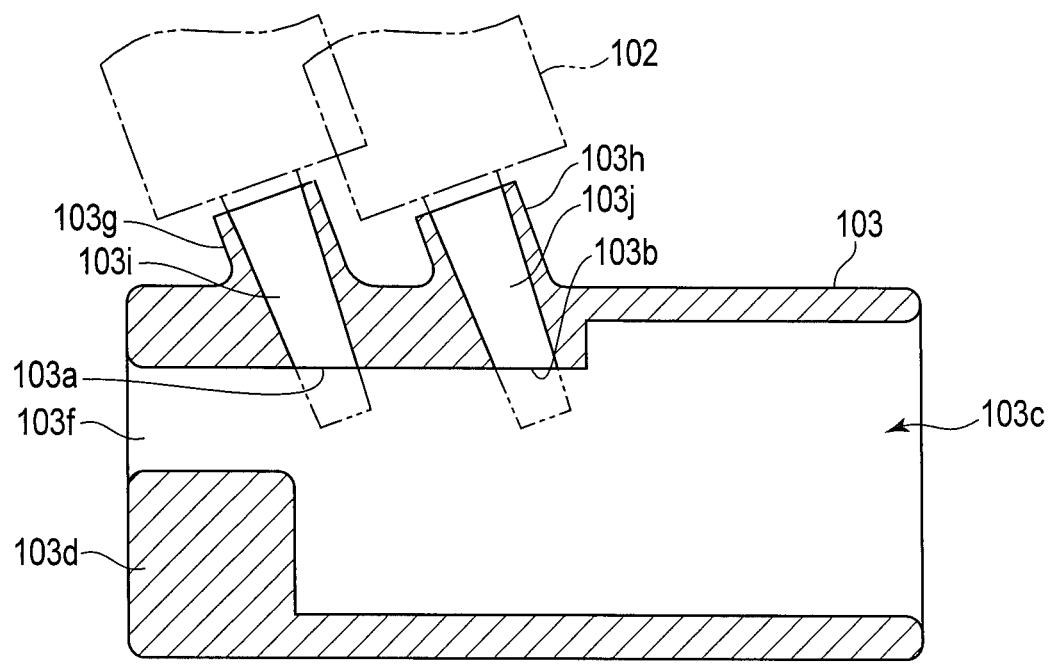
F I G. 15B

WASHING INSTRUMENT FOR INSERTION DEVICE

CROSS-REFERENCE TO RELATED APPLICATIONS

This is a Continuation Application of PCT Application No. PCT/JP2015/075910, filed Sep. 11, 2015, which was published under PCT Article 21(2) in Japanese.

This application is based upon and claims the benefit of priority from prior the Japanese Patent Application No. 2014-210879, filed Oct. 15, 2014 the entire contents of which are incorporated herein by references.

BACKGROUND OF THE INVENTION

1. Field of the Invention

The present invention relates to a washing instrument for an insertion device in which a treatment instrument swing base is disposed on a distal side.

2. Description of the Related Art

In general, a treatment instrument having various functions, e.g., a forceps is inserted from an endoscope main body into a channel of an inserting section, and extends out from an aperture section opened on a distal side. Furthermore, there is known a swing mechanism disposed in a treatment instrument receiving chamber in the aperture section provided in a part of an inserting section distal end on its peripheral surface side, to turn, in a desirable direction, a traveling direction of the treatment instrument that extends out from the aperture section. As a typical swing mechanism, a swing base for the treatment instrument (or a treatment instrument raising base) is known. This swing base abuts on the treatment instrument such as the forceps, and is raised by operating an operation lever provided on an operating section side, so that it is possible to change the traveling direction of the treatment instrument to the desirable direction.

Furthermore, when the inserting section is inserted into a body cavity, a body fluid, a resected living tissue and the like intrude into the receiving chamber from an opening portion in which the swing base is disposed, to adhere to a swing base main body and its peripheral portion. After end of a treatment, washing and disinfection are essential for an endoscope to prevent infection.

For example, in Patent Literature 1: Jpn. Pat. Appln. KOKAI Publication No. H08-196505, there has been suggested a technology on washing in a distal portion of an inserting section of an endoscope. In a front surface of the distal portion of the inserting section of the endoscope, an attaching portion is formed to communicate with a treatment instrument receiving chamber and attach a washing instrument to the attaching portion. A connecting section of the washing instrument which is attached to this attaching portion has a flow channel to feed and suck a washing liquid, and the washing liquid is fed into and sucked from the receiving chamber through this flow channel to remove dirt in the receiving chamber. In this constitution, the washing is performed in a state of directly inserting the connecting section of the washing instrument, and hence to prevent the washing liquid in use from leaking or flying and scattering, it is required to maintain a securely connected state.

In this cited literature 1, as another example, a cover member has been suggested which covers the whole distal portion of an inserting section so that a connecting section is hard to be disconnected. When the whole distal portion is covered with the cover member, the connecting section is attached in a state of inserting the connecting section into an attaching port via the cover member. Furthermore, in this cover member, a drain opening is formed to expose the aperture section of the receiving chamber to the outside when attaching the connecting section.

BRIEF SUMMARY OF THE INVENTION

According to an embodiment of the present invention, there is provided a washing instrument for an insertion device comprising: a washing instrument main body having a tubular hollow receiving portion that receives a distal end constituting section of the insertion device; a liquid feed mechanism that feeds a washing fluid from the outside into the receiving portion; washing ports which are provided away from one another in an inner peripheral surface of the receiving portion and from which the fluid fed from the liquid feed mechanism jets out indirections which intersect a longitudinal axis direction of the receiving portion and which are different from one another; a movement regulating portion that positions the distal end constituting section at a position at which the fluid jetting out from the washing port directly collides with each desirable washing target region in an aperture section provided in the distal end constituting section received in the receiving portion; and a movement regulating portion that positions the distal end constituting section at a position at which the fluid jetting out from the washing port directly collides with each desirable washing target region in an aperture section provided in the distal end constituting section received in the receiving portion; and a holding portion that holds a positioned state of the distal end constituting section by the movement regulating portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2A is a top view of a distal end constituting section in the first embodiment;

FIG. 2B is a front view of the distal end constituting section seen from the side of an arrow 2B shown in FIG. 2A;

FIG. 4B is a view showing a state where an insertion device is attached to the washing instrument and washed;

FIG. 5 is a view of the washing instrument to which the insertion device is not attached and which is seen from a front surface side;

FIG. 10 is a view showing a transverse section of a washing instrument main body to which an insertion device is attached according to a fifth embodiment;

FIG. 12 is a view showing an appearance constitution of a syringe for use in a washing instrument according to a seventh embodiment;

FIG. 13A is a view showing a transverse section of a washing instrument main body to which an insertion device is attached;

FIG. 15A is a view showing an appearance constitution of a syringe for use in a washing instrument according to an eighth embodiment; and FIG. 15B is a view showing a transverse section of a washing instrument main body to which the syringe is attached.

DETAILED DESCRIPTION OF THE PREFERRED EMBODIMENT

Hereinafter, embodiments of the present invention will be described in detail with reference to the drawings.

First Embodiment

A washing instrument for an insertion device according to a first embodiment will be described.

Figure 1:
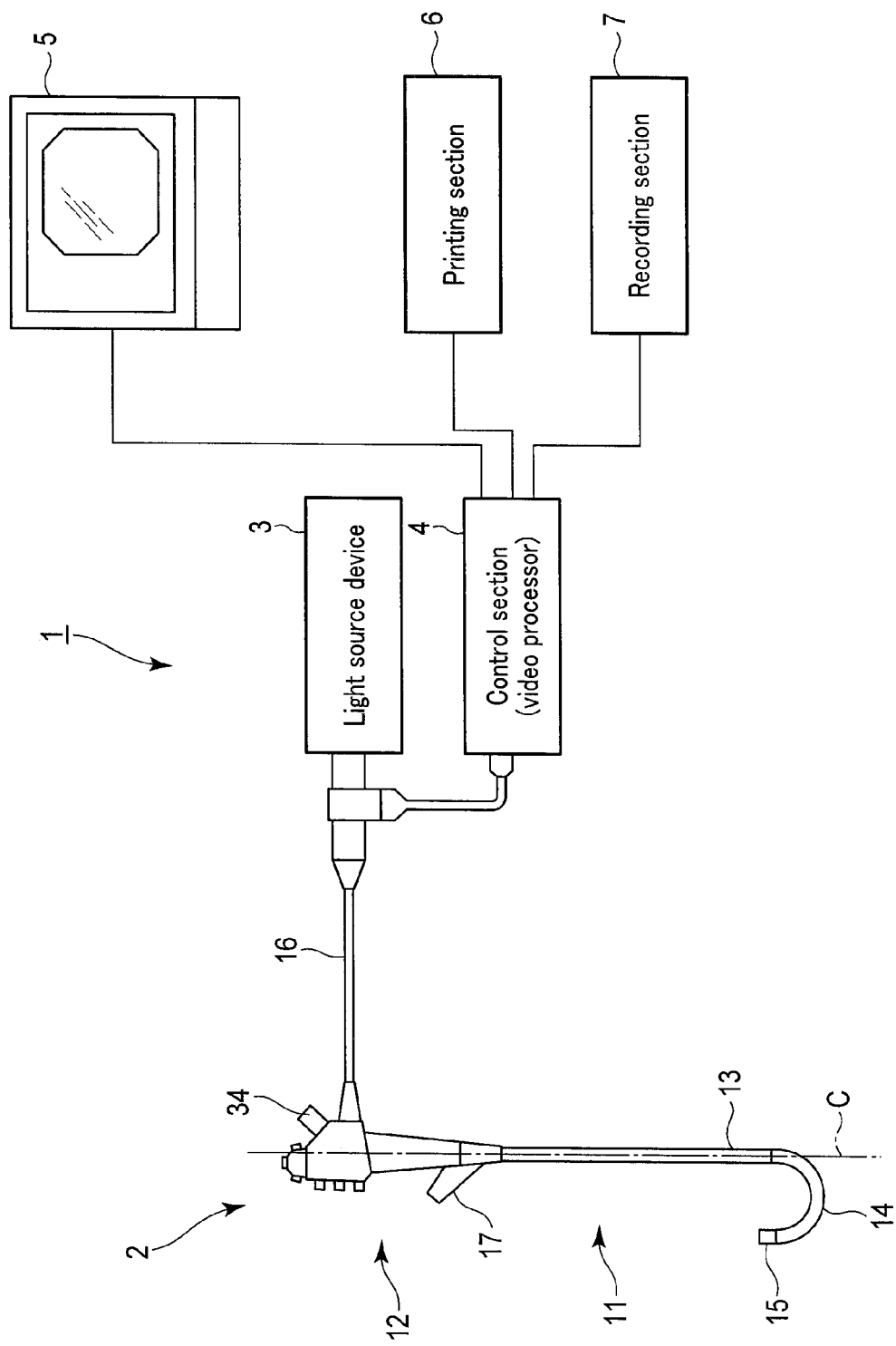
FIG. 1 is a schematic view of an insertion system according to a first embodiment of the present invention.
Figure 3:
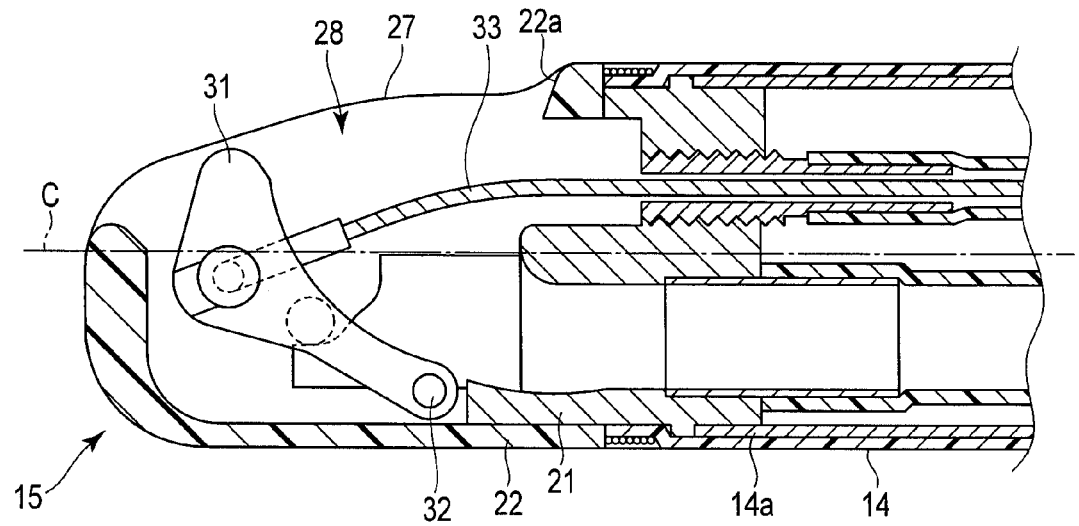
FIG. 3 is a view showing a constitution of a transverse section of a swing base having an inverted state in the distal end constituting section shown in FIG. 2A.

First, there will be described a distal portion including a treatment instrument swing base (hereinafter referred to as the swing base) provided at a distal end of an inserting section of an endoscope apparatus, as one example of a washing target of the washing instrument of the present embodiment. FIG. 1 is a view showing a system constitution of the endoscope apparatus that is the washing target. FIG. 2A is a top view of a distal end constituting section including the swing base provided at a distal end of the insertion device, and FIG. 2B is a view showing an appearance constitution of the distal end constituting section seen from a front surface. FIG. 3 is a view showing a constitution of a transverse section of the swing base having an inverted state in the distal end constituting section shown in FIG. 2A.

As shown in FIG. 1, an endoscope apparatus 1 is mainly constituted of an insertion device 2 that is an endoscope main body, a light source device 3 that supplies illumination light to the insertion device 2, a control section 4 including a video processor that performs image processing to a video signal imaged by an unshown imaging unit disposed in a distal portion of the insertion device 2, a display section 5 that displays a photographed observation image and information on the image, a printing section 6 that prints the image information including the observation image displayed in the display section 5, and a recording section 7 that records the video signal. Here, the medical endoscope apparatus is defined as one example of the insertion device, but does not have to be limited to this example. Additionally, the insertion device 2 can be washed by a washing instrument of the present embodiment as long as the insertion device 2, for example, a catheter, an over tube or the like which does not have an industrial endoscope, an illumination optical system and an observation optical system, and has a constitution in which an aperture section or a region that is the washing target is inserted and removed from a peripheral surface side.

As shown in FIG. 1, the insertion device 2 is mainly constituted of an inserting section 11 and an operating section 12. The inserting section 11 has a flexible tube portion 13 coupled with the operating section 12 and having flexibility, a bending portion 14 coupled with a distal end of the flexible tube portion 13, and a distal end constituting section 15 provided at a distal end of the bending portion 14 to receive the swing base. The operating section 12 is connected to the light source device 3 and the control section 4 by a universal cord 16. A forceps port 17 to introduce forceps or the like into the inserting section is interposed between a proximal portion of the inserting section 11 and the operating section 12.

As shown in FIG. 3, a node ring 14a of the bending portion 14 is fitted into the distal end constituting section 15 that is the distal portion of the insertion device, to couple the distal end constituting section with the bending portion 14. The distal end constituting section 15 is a laminated structure in which a main body portion 21 is made of a metal such as SUS, and further, a peripheral surface of the main body portion 21 is covered with a cover portion 22 having electric insulating properties.

As shown in FIG. 2A and FIG. 2B, a part of an outer peripheral surface of the distal end constituting section 15 is flattened, and the flattened portion is divided into two sides in a longitudinal axis direction, and on one side, a stepped portion 25a is provided from the outer peripheral surface to form a flat observation surface 25, and on the other side, an aperture section 27 is formed. In the observation surface 25, there are arranged an illumination window portion 23 to be irradiated with the illumination light and an observation window portion 24 including therein an unshown imaging element. In the vicinity of the observation surface 25, a nozzle portion 26 is disposed from which a washing liquid such as saline jets outside, thereby suitably washing the illumination window portion 23 and the observation window portion 24. It is to be noted that the observation surface 25 is a reference position (a reference surface) to an after-mentioned rotating direction regulating portion 42h.

Furthermore, as shown in FIG. 3, the aperture section 27 on the other side opens in a side peripheral surface of the distal end constituting section 15. In a receiving chamber (or a swing base receiving chamber) 28 in the aperture section 27, a treatment instrument swing base (hereinafter referred to as the swing base) 31 is swingably disposed. Character C shown in FIG. 1 and FIG. 3 shows a direction in which the inserting section 11 and the distal end constituting section 15 are longitudinal, and indicates the longitudinal axis direction.

By a drive mechanism constituted of a turnably supporting raising shaft 32, a traction wire 33 coupled with the swing base 31 at one end, and a raising operation portion 34 coupled with the other end of the traction wire 33 and provided in the operating section 12, the swing base 31 turns to be raised or inverted. In this way, the swing base 31 and its drive mechanism are arranged in the narrow receiving chamber 28, and hence it is hard to remove dirt due to a body fluid or a living tissue piece adhered to a region that is shade seen from the aperture section 27, e.g., a periphery of the raising shaft 32, a back surface of the swing base 31, or the like. The swing base 31 is not limited to the raising type, but may be a type of horizontally swinging a treatment instrument.

Next, a washing instrument 41 according to the first embodiment will be described.

Figure 4A:
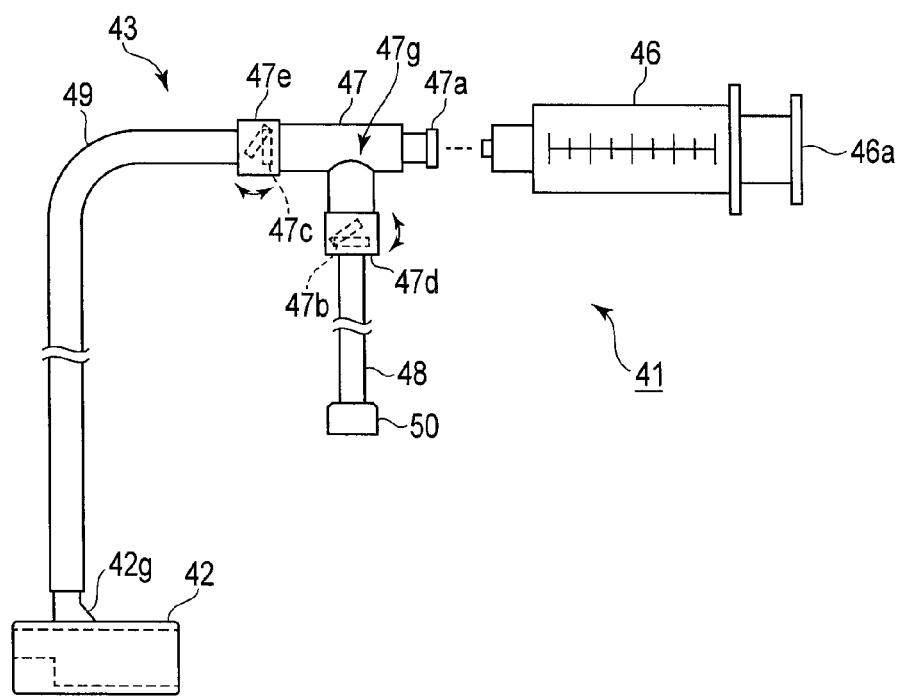
FIG. 4A is a view showing an appearance constitution of a washing instrument of the first embodiment.
Figure 6A:
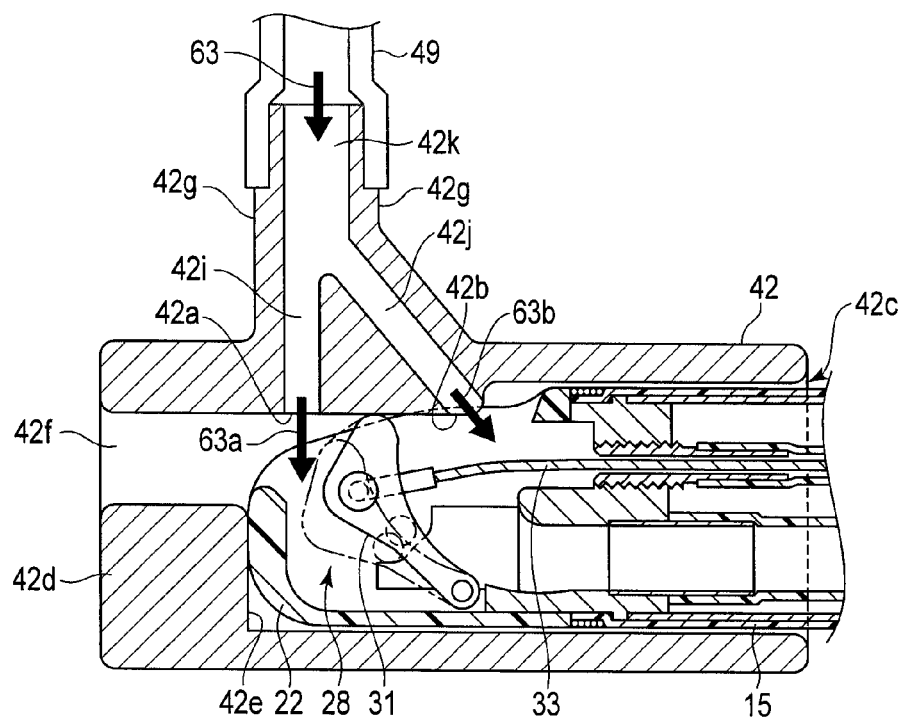
FIG. 6A is a view showing a transverse section of a washing instrument main body to which the insertion device is attached.
Figure 6B:
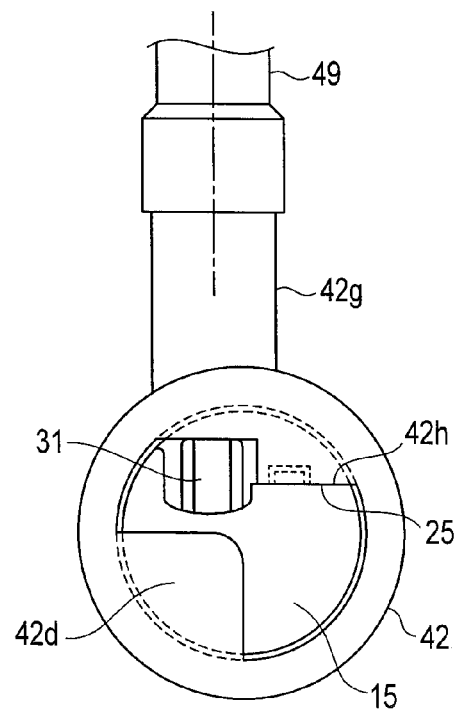
FIG. 6B is a view of the washing instrument main body to which the insertion device is attached and which is seen from a front side.

FIG. 4A is a view showing an appearance constitution of the washing instrument of the present embodiment, FIG. 4B is a view showing a state where the insertion device is attached to the washing instrument and washed, FIG. 5 is a view of a washing instrument main body seen from a front side, FIG. 6A is a view showing a transverse section of the washing instrument to which the insertion device is attached, and FIG. 6B is a view of the washing instrument to which the insertion device is attached and which is seen from the front side. In the washing instrument mentioned below, a side into which the distal end constituting section 15 of the distal portion of the insertion device is inserted is defined as a rear side of the washing instrument, and a side on which a distal portion of the distal end constituting section 15 is defined as a front side.

The washing instrument 41 of the present embodiment is roughly constituted of a washing instrument main body 42 and a liquid feed mechanism 43. The washing instrument main body 42 uses a transparent member and has a hollow receiving portion to which the distal end constituting section 15 is attached. The liquid feed mechanism 43 has an injection tube 49 coupled with a joint portion 42g of the washing instrument main body 42, a syringe coupling portion 47 coupled with the injection tube 49, a suction tube 48 extending from a branching liquid suction end 47d of the syringe coupling portion 47, a tubular weight 50 that prevents lift and also serves as a water suction port of the suction tube 48, and a syringe 46 of pumping means through which a washing fluid flows. It is preferable that the washing instrument 41 including the washing instrument main body 42 and mentioned below is prepared by using a transparent member. The use of the transparent member makes it easy to confirm a removal degree of the dirt from the outside. Furthermore, the injection tube 49 and the washing instrument main body 42 form an attachable/detachable structure, whereby when the washing instrument main body 42 is prepared in accordance with a shape of a distal portion of any insertion device, the washing instrument is usable as a washing instrument having high general-purpose properties.

The syringe coupling portion 47 forms a T-shape branching in three ways, a storage chamber (a space to temporarily store a washing liquid 63) 47g is formed in the syringe coupling portion, the opening liquid suction end 47d and an opening liquid feed end 47e are provided in two of three end portions, and check valves 47b and 47c are disposed in the ends, respectively. Another end portion is a syringe attaching end 47a to be coupled with the syringe 46. A combination of the syringe 46 and the syringe coupling portion 47 functions as a pump. The check valves 47b and 47c may have a known structure in which a valve portion moves to close and open the flow channel, and may have, for example, a constitution in which a C-shaped slit is cut in a circular partition plate constituted of an elastic member so that the valve portion has a diameter larger than the flow channel.

In the syringe coupling portion 47 shown in FIGS. 4A and 4B, in the liquid feed end 47e, there is provided the check valve 47c adjusted into an opened state by turning the valve portion toward the outside when an inner pressure of a coupling portion main body is a positive pressure, and adjusted into a closed state by sucking the valve portion with a valve seat when the inner pressure is a negative pressure. Furthermore, in the liquid suction end 47d, there is provided the check valve 47b adjusted into an opened state by turning the valve portion inwardly when the inner pressure of the coupling portion main body is the negative pressure, and adjusted into a closed state by pressing the valve portion onto the valve seat when the inner pressure is the positive pressure. This is because a plunger 46a of the syringe 46 is pulled outside to adjust the inner pressure of the coupling portion main body into the negative pressure, the washing liquid 63 flows into the storage chamber 47g and the syringe 46, the plunger 46a is pushed inside to adjust the inner pressure of the coupling portion main body into the positive pressure, and the washing liquid 63 flows out from the storage chamber 47g and the syringe 46. In place of the syringe that feeds the washing liquid 63, liquid feed means such as a liquid feed pump may be used.

Washing of the insertion device with the washing instrument 41 of the present embodiment will be described.

FIG. 4B shows a state of attaching the distal end constituting section 15 of the insertion device 2 to the washing instrument 41. The distal end constituting section 15 is positioned as described later and attached to the washing instrument main body 42 of the washing instrument 41, and the washing instrument is disposed in a drain tray 61. At this time, a liquid such as water is beforehand put in the drain tray 61, and the washing instrument main body 42 is sunk in the tray, so that in a case of discharging the washing liquid 63 from an opening 42f with great energy, it is possible to weaken the energy with the liquid and prevent the washing liquid from flying and scattering around the drain tray 61. Furthermore, a tray cover to prevent the flying and scattering may separately be prepared. It is to be noted that at least the drain tray 61 is prepared by using the transparent member. The use of the transparent member makes it easy to confirm the removal degree of the dirt from the outside. In the washing instrument main body 42, its outer shape is cylindrical, but there is not any restriction on the outer shape as long as an inner shape is a hollow shape to which the distal end constituting section 15 is attachable, and the outer shape may be a rectangular box shape.

Next, a water suction port 50 of the suction tube 48 is disposed to sink in a suction water tray 62 filled with the washing liquid 63. The plunger 46a of the syringe 46 is pulled to pump up the washing liquid 63 in the suction water tray 62, thereby filling the storage chamber 47g of the syringe coupling portion 47 and the syringe 46. Furthermore, the plunger 46a is pushed to feed the washing liquid from the injection tube 49 to the washing instrument main body 42, and the washing liquid is supplied (here, jets out) from two after-mentioned washing ports at different angles, to wash the inside of the receiving chamber 28 including the swing base. The used washing liquid 63 is discharged together with adhered substances from the receiving chamber 28 through the opening (the opening 42f shown in FIG.

6A) to the drain tray 61. Furthermore, simultaneously, the washing liquid 63 flowing out from the receiving chamber 28 passes through an after-mentioned clearance while washing a peripheral portion of the distal end constituting section 15 attached to the washing instrument main body 42, and the washing liquid is discharged to the drain tray 61.

The washing instrument main body 42 will be described with reference to FIGS. 6A and 6B.

The washing instrument main body 42 of the present embodiment is a constitution in which one flow channel 42k in the joint portion 42g coupled with the injection tube 49 to become a supply receiving port of the washing liquid 63 branches into two flow channels 42i and 42j at the different angles in the main body and first and second washing ports 42a and 42b are arranged at distal ends of the respective flow channels.

In this example, it is described that the washing liquid jets out from the first washing port 42a in a direction perpendicular to the longitudinal axis direction of the distal end constituting section 15. Furthermore, the washing liquid jets out from the second washing port 42b obliquely in a downward direction from a front side toward a rear side of a distal portion of the port. Needless to say, there is not any restriction on the directions in which the washing liquids jet out from the first and second washing ports 42a and 42b, and the directions may suitably be changed by design.

In the washing instrument main body 42, an insertion port 42c to insert the distal end constituting section 15 is provided on the rear side, an axial direction regulating portion 42d (a first movement regulating portion) abutting on the distal end constituting section 15 is provided on the front side, and in an upper portion of an inner peripheral surface, there are provided the rotating direction regulating portion 42h (a second movement regulating portion) facing the observation surface 25 of the distal end constituting section 15 described above, and the opening 42f to discharge the used washing liquid 63 to the outside.

The axial direction regulating portion 42d and the rotating direction regulating portion 42h constitute the movement regulating portions, thereby positioning the distal end constituting section 15 at a predetermined attaching position in the washing instrument main body 42. It is to be noted that the attaching position is adjusted into a position at which the washing liquid 63 jetting out from the first and second washing ports 42a and 42b directly collides with a washing target region in the receiving chamber 28.

In the present embodiment, drain water of the washing liquid 63 used in washing may be discharged through the clearance between the outer peripheral surface of the distal end constituting section 15 and the inner peripheral surface of the washing instrument main body 42, in addition to the opening 42f. Furthermore, in a case where a drain amount of the washing liquid 63 is large to such an extent that cannot be covered with the clearance, a drainable concave groove type of clearance (not shown) may be formed in a part of the inner peripheral surface along the inner peripheral surface in the longitudinal axis direction.

As shown in FIG. 6A, the distal end constituting section 15 is inserted from the insertion port 42c into the washing instrument main body 42, and its distal end abuts on a positioning wall 42e of the axial direction regulating portion 42d while disposing the observation surface 25 to face the rotating direction regulating portion 42h, whereby the distal end constituting section 15 is positioned in an axial direction and a rotating direction. Afterward, by an operation of the raising operation portion 34, a distal portion of the swing base 31 rises to be positioned between the first washing port 42a and the second washing port 42b, and abuts on the inner peripheral surface of the washing instrument main body 42, to hold a positioned state.

The distal portion of the swing base 31 is referred to as a holding portion to hold the positioned state, and the inner peripheral surface of the washing instrument main body 42 which abuts on this distal portion is referred to as a holding surface. This holding surface constitutes a swing base angle regulating portion set at an intermediate position between a position at which the swing base 31 completely falls and a position at which the swing base completely rises, to position the swing base 31. It is to be noted that the washing instrument main body 42 is made of a transparent resin or the like, whereby even when the swing base 31 abuts on an upper inner surface of the washing instrument main body 42, the swing base 31 is not impaired.

There will be described the flow channels 42k, 42i and 42j and the first and second washing ports 42a and 42b of the washing instrument main body 42. It is to be noted that in the embodiment, the washing port is provided at the distal end of each linear flow channel, and hence a constitution is illustrated in which the flow channel is disposed at an angle from a branching region, but there is not any special restriction on a flow channel route itself as long as the washing ports are provided to vary a jetting direction of the washing liquid 63 and a position reached by the washing liquid 63. Furthermore, diameters of the flow channels may be adjusted so that the diameters of the flow channels 42i and 42j decrease to taper off from the flow channel 42k of an inflow port to the first and second washing ports 42a and 42b, thereby increasing a jetting pressure of the jetting washing liquid 63. Furthermore, the first and second washing ports 42a and 42b narrow to function as nozzles, so that it is possible to increase the jetting pressure of the jetting washing liquid 63.

As shown in FIG. 6A, in the main body, the flow channel 42k branches into at least two flow channels 42i and 42j, and an optional inclination due to an angle difference is interposed between the flow channel 42i and the flow channel 42j in the axial direction to vary a liquid feed direction (a jetting angle) of the washing liquid 63 in the branching region. The first and second washing ports 42a and 42b are opened as respective flow channel distal ends via a space on the main body inner peripheral surface so that washing liquids 63a and 63b jet out into the receiving chamber 28 at different jetting angles from the aperture section 27 of the distal end constituting section 15 into the receiving chamber 28.

The washing liquid 63a jets out from the first washing port 42a directly to the washing target region in a range from a back side of the surface of the receiving chamber 28 of the distal end constituting section 15 which comes in contact with a front side surface (the positioning wall 42e) through a bottom surface to a back surface side of the rising swing base 31. Furthermore, the washing liquid 63b jets out from the second washing port 42b directly toward a washing target region such as a rear side and the bottom surface of the receiving chamber 28, a periphery of the raising shaft 32 of the swing base 31, or the traction wire 33. Here, the washing liquids 63 jet out from the first washing port 42a and the second washing port 42b to the receiving chamber 28 of the distal end constituting section 15 in the directions both of which intersect the longitudinal axis of the insertion device 2 and which are different from each other (or at the different jetting angles).

Furthermore, the washing instrument main body 42 is a constitution in which both front and rear ends are opened, and not only the opening 42f of the distal end but also the clearance from the washing instrument main body 42 which is large as described above are disposed to the distal end constituting section 15 of an insertion device such as an endoscope, so that the used washing liquid 63 or filth is easy to flow outside. It is to be noted that in the present embodiment, there has been described a constitutional example in which the washing ports are provided in two regions of the first and second washing ports 42a and 42b, but the washing ports may be provided in two or more regions.

As described above, according to the present embodiment, the state of positioning the distal end constituting section 15 of the insertion device 2 is held, and the washing liquids 63 jet out from the first washing port 42a and the second washing port 42b which are arranged away from each other to the receiving chamber 28 of the distal end constituting section 15 in the mutually different directions (or at the different jetting angles), so that the washing liquid 63 can directly jet out to various regions including the swing base 31 disposed in the receiving chamber 28 with respective high water feed forces, thereby performing the washing.

In this way, the washing liquids 63 jetting out from the regions at the different angles not only directly collide with the washing target regions but also generate a complicated water flow in the receiving chamber 28, thereby achieving more effective washing. It is to be noted that the jetting angles from the washing ports which are present at different positions may be the same.

Furthermore, even when the attached washing instrument main body 42 unintentionally shifts or comes outside, the distal end constituting section 15 is tubularly covered, the washing liquids 63a and 63b jetting out from the first washing port 42a and the second washing port 42b collide with the inner peripheral surface (the wall surface) of a part of the washing instrument main body 42, and flow in the longitudinal axis direction to remain in the drain tray 61, and hence the washing liquid 63 does not directly spray over an operator. Furthermore, the washing instrument main body 42 sinks in water to perform the washing, thereby discharging the used washing liquid 63 into the water, and even when the distal end constituting section 15 comes out from the washing instrument main body 42, it is possible to prevent the used washing liquid 63 from flying and scattering to the outside. Furthermore, the injection tube 49 and the washing instrument main body 42 constitute the attachable/detachable structure, whereby when the washing instrument main body is only prepared in accordance with the shape of the distal portion of any insertion device, the washing instrument having high general-purpose properties is usable.

Second Embodiment

Figure 7:
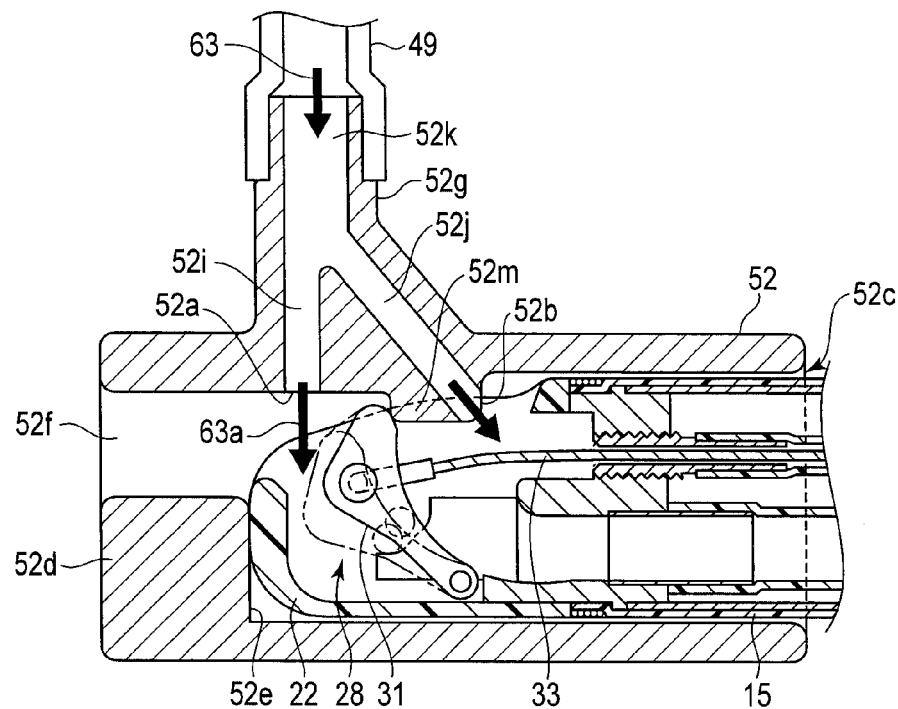
FIG. 7 is a view showing a transverse section constitution of a washing instrument main body according to a second embodiment.

FIG. 7 is a view showing a transverse section constitution of a washing instrument main body according to a second embodiment. The present embodiment is different from the above-mentioned first embodiment only in that a fixing system of a distal end constituting section 15, and the other constitutional region is equivalent to the above-mentioned first embodiment. In the above-mentioned first embodiment, for the purpose of holding positioning of the distal end constituting section 15, a swing base 31 rises to bring a distal portion of the swing base 31 into contact with a flat inner peripheral surface of a washing instrument main body 42 which is a holding surface.

In the present embodiment, as shown in FIG. 7, an locking portion 52m of a convex shape is formed in a region of a holding surface of a washing instrument main body 42 to engage a raised distal portion of a swing base 31 with a corner of the locking portion. In this constitution, the corner of the locking portion 52m is formed between a first washing port 42a and a second washing port 42b, and has a projecting shape including the second washing port 42b.

The distal portion of the swing base 31 rises to engage with this corner of the locking portion 52m, whereby the distal end constituting section 15 advances to press its distal surface onto a positioning wall 52e, thereby holding a positioned state of the distal end constituting section 15.

As described above, in a washing instrument of the present embodiment, in addition to the above-mentioned operation and effect of the first embodiment, the distal end constituting section 15 of an insertion device is inserted and positioned, and then the distal portion of the swing base 31 rises to engage with the locking portion 52m, thereby pressing and locking both sides of the locking portion 52m and the positioning wall 52e, so that it is possible to hold the positioned state of the distal end constituting section 15.

Third Embodiment

Figure 8:
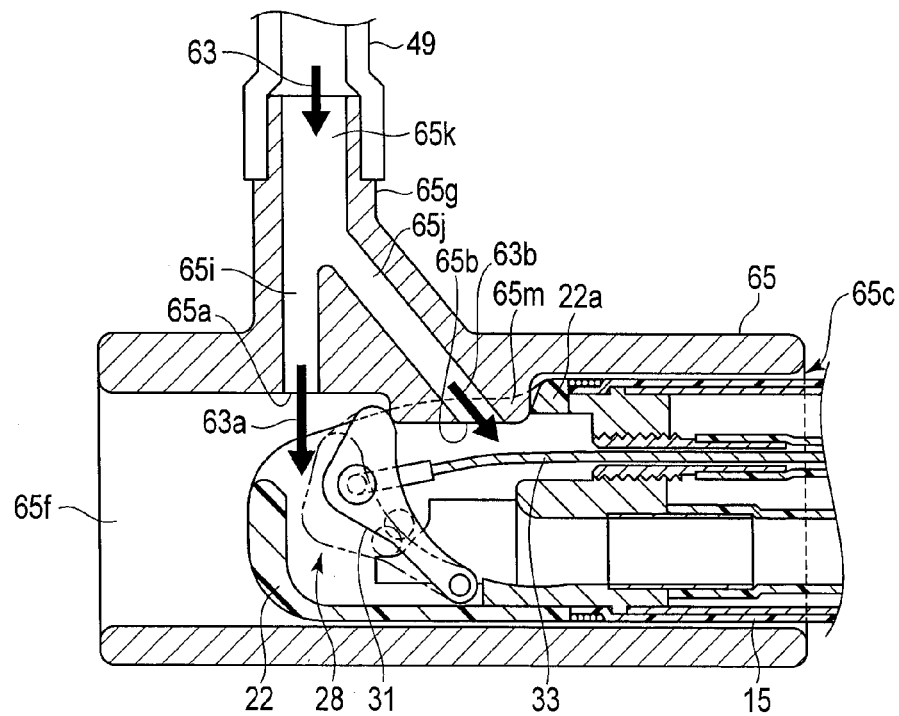
FIG. 8 is a view showing an appearance constitution of a washing instrument main body for an insertion device according to a third embodiment.

FIG. 8 is a view showing an appearance constitution of a washing instrument main body for an insertion device according to a third embodiment. The present embodiment is a constitution in which there is changed a forming position of an axial direction regulating portion in the washing instrument main body of the above-mentioned first and second embodiments, and this axial direction regulating portion is also utilized as an locking portion in the above-mentioned second embodiment. Both front and rear sides of an axial direction regulating portion 65m of a washing instrument main body 65 are sandwiched between a cover portion 22a on a proximal side of an aperture section 27 of a distal end constituting section 15 and a distal portion of a swing base 31, thereby holding a positioned state. In the present embodiment, a constitution other than a holding region of the positioned state is equivalent to the above-mentioned second embodiment.

The washing instrument main body 65 of the present embodiment forms a cylindrical shape opening forward and backward, and in its outer peripheral surface, a joint portion 65g coupled with an injection tube 49 is provided. One flow channel 65k in the joint portion 65g branches into two flow channels 65i and 65j at different angles in the main body, and at respective flow channel distal ends, first and second washing ports 65a and 65b are provided. The first and second washing ports 65a and 65b are provided to open in two regions via a space in a main body inner peripheral surface at the respective flow channel distal ends, so that washing liquids 63a and 63b jet out into a receiving chamber 28 at different jetting angles from the aperture section 27 of the distal end constituting section 15 into the receiving chamber. FIG. 8 illustrates an example in which the washing liquid 63a jetting out from the first washing port 65a jets out in a direction perpendicular to a longitudinal axis direction of the distal end constituting section 15.

On the inner peripheral surface of the washing instrument main body 65, the axial direction regulating portion 65m of a projecting shape is provided to abut on the cover portion 22a on the proximal side of the aperture section 27, when the distal end constituting section 15 is inserted from an insertion port 65c. This providing position of the axial direction regulating portion 65m is a position at which the cover portion 22a abuts on a corner of a rear end of the axial direction regulating portion 65m, and is set so that the washing liquids 63a and 63b jet out to equivalent positions in the receiving chamber 28 at the same jetting angles (of the washing ports 65*a* and 65*b* in the present embodiment) as in the first and second washing ports 42*a* and 42*b* of the above-mentioned first embodiment. Furthermore, similarly to the locking portion 52*m* in the above-mentioned second embodiment, when the distal portion of the swing base 31 rises to engage with a corner on a front side of the axial direction regulating portion 65*m*, the distal end constituting section 15 is pushed to press the corner by the cover portion 22*a*. Consequently, the front and rear corners of the axial direction regulating portion 65*m* are sandwiched between the cover portion 22*a* and the distal portion of the swing base 31, and the washing instrument main body 65 held in the positioned state is attached to the distal end constituting section 15.

In addition to the above-mentioned operation and effect of the second embodiment, in the washing instrument of the present embodiment having this constitution, the axial direction regulating portion 65*m* moves inward from a front surface of the washing instrument main body 65, and hence a distal portion of the distal end constituting section 15 does not have to abut, so that it is possible to apply the washing instrument even to an insertion device that is not suitable for the abutment of the distal portion. Furthermore, the axial direction regulating portion 65*m* is positioned by bringing its corner on the rear side into contact with the cover portion 22*a* on the proximal side of the aperture section 27 of an insertion device 2, and furthermore, the axial direction regulating portion 65*m* is sandwiched by attaching its corner on the front side to the raised distal portion of the swing base 31, so that it is possible to hold a positioned state of the distal portion of the distal end constituting section 15. In a case of discharging a used washing liquid 63, the whole front surface of the washing instrument main body 52 becomes an opening to discharge the washing liquid 63, and hence it is possible to also cope with increase of an amount of the washing liquid 63 to be discharged.

Fourth Embodiment

Figure 9:
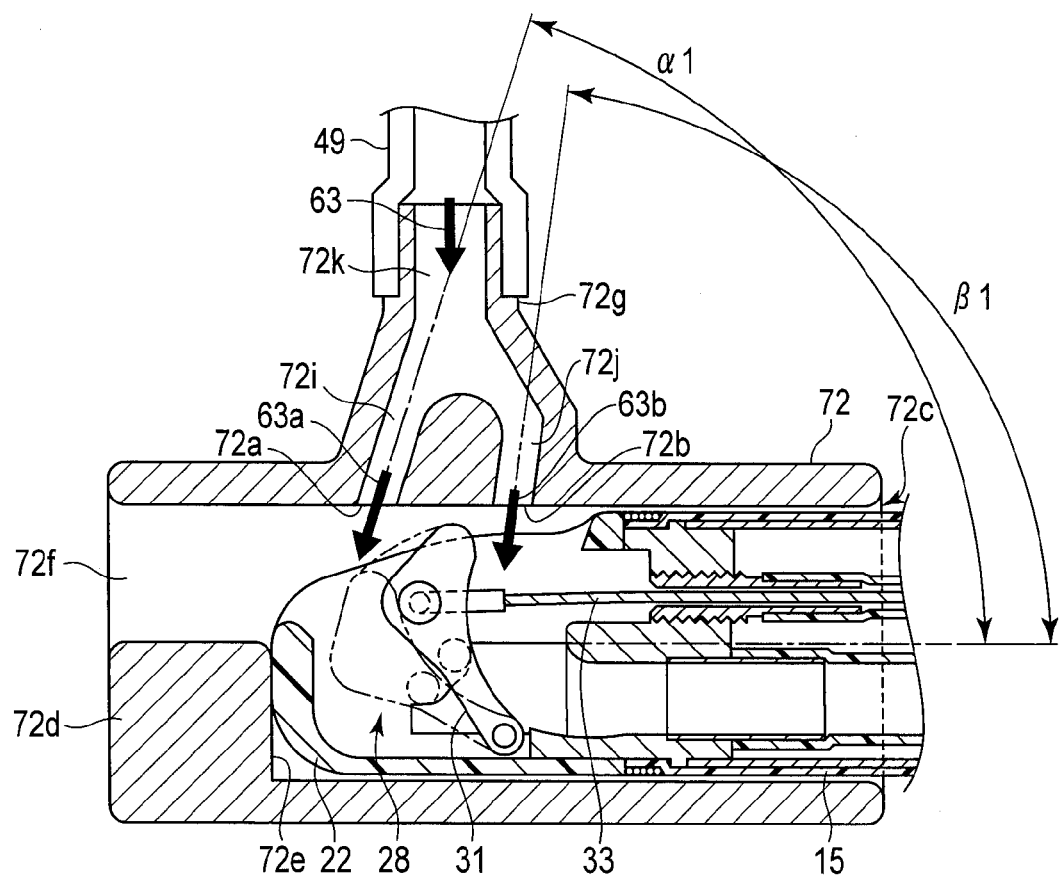
FIG. 9 is a view showing a transverse section of a washing instrument main body to which an insertion device is attached according to a fourth embodiment.

FIG. 9 is a view showing a transverse section of a washing instrument main body to which an insertion device is attached according to a fourth embodiment. The present embodiment is a constitution to hold a positioned state of a distal portion of a distal end constituting section 15 by a pressure of a washing liquid 63 jetting out from first and second washing ports of the washing instrument main body. In the present embodiment, a constitution other than flow channels 72*i* and 72*j* and first and second washing ports 72*a* and 72*b* of the washing instrument main body is equivalent to the above-mentioned first embodiment.

A washing instrument main body 72 of the present embodiment is a constitution in which one flow channel 72*k* in a joint portion 72*g* coupled with an injection tube 49 to become a supply receiving port of the washing liquid 63 branches into two flow channels 72*i* and 72*j* at different angles in the main body, to feed the liquid to each of the first and second washing ports 72*a* and 72*b*.

In this example, the flow channel 72*i* extends obliquely downward from a rear side toward a front side at an acute angle set to an angle $\alpha 1$, and the flow channel 72*j* similarly extends obliquely downward from the rear side toward the front side at the acute angle set to an angle $\beta 1$ which is larger than the angle $\alpha 1$ (wherein the angle is smaller than 90 degrees). In the present embodiment, a direction in which a washing liquid 63*a* jets out from the first washing port 72*a* and a longitudinal axis direction of the flow channel 72*i* are present on the same axis, and a jetting angle is identical to the angle $\alpha 1$. Furthermore, a direction in which a washing liquid 63*b* jets out from the second washing port 72*b* and a longitudinal axis direction of the flow channel 72*j* are present on the same axis, and a jetting angle is identical to the angle $\beta 1$.

The washing liquids 63*a* and 63*b* jetting out from the first and second washing ports 72*a* and 72*b* collide with predetermined positions (the same colliding positions as in the first embodiment) of a receiving chamber 28 of the distal end constituting section 15, to perform washing. Specifically, the washing liquid 63*a* jetting out from the first washing port 72*a* directly sprays on a range from a front side surface and a bottom surface of the receiving chamber 28 to a back surface side of a swing base 31 to perform the washing. Furthermore, the washing liquid 63*a* jetting out from the second washing port 72*b* directly sprays on a raised surface of the swing base 31, a rear side and the bottom surface of the receiving chamber 28, a periphery of a raising shaft 32 of the swing base 31, an attaching region of a traction wire 33, and the like to perform the washing.

According to such a constitution, in a washing instrument of the present embodiment, pressures due to the jetting washing liquids 63*a* and 63*b* act in a direction to press the receiving chamber 28 of the distal end constituting section 15 onto an axial direction regulating portion 72*d*, to hold a positioned state of the distal portion of the distal end constituting section 15.

Furthermore, a direction in which the pressure due to the washing liquid 63*b* acts (the angle $\beta 1$) has an angle larger than a direction in which the pressure due to the washing liquid 63*a* acts (the angle $\alpha 1$). That is, the washing liquids 63*a* and 63*b* jet out at the different angles, whereby the pressure due to the washing liquid 63*a* has a high ratio of a force that acts in a direction to press the receiving chamber 28 onto the axial direction regulating portion 72*d*, and the pressure due to the washing liquid 63*b* has a high ratio of a force that acts in a direction to press the receiving chamber 28 onto an inner peripheral surface side of the washing instrument main body. Therefore, it is possible to press the receiving chamber onto the axial direction regulating portion 72*d* by the pressure of the washing liquid 63*a*, and it is possible to prevent lift of the distal end constituting section 15 by the pressure of the washing liquid 63*b*. Needless to say, there is not any restriction on the angles concerning the directions in which the washing liquids jet out from the first and second washing ports 72*a* and 72*b*, and the angles are suitably changed by design. When the pressures due to the jetting washing liquids 63*a* and 63*b* work in the direction to press the receiving chamber 28 of the distal end constituting section 15 onto the axial direction regulating portion 72*d*, the acute angles $\alpha 1$ and $\beta 1$ may be the same angle.

Fifth Embodiment

FIG. 10 is a view showing a transverse section of a washing instrument main body to which an insertion device is attached according to a fifth embodiment. Similarly to the above-mentioned fourth embodiment, the present embodiment is a constitution to hold a positioned state of a distal portion of a distal end constituting section 15 by a water feed force (a pressure) of a washing liquid 63 jetting out from first and second washing ports of the washing instrument main body. In the present embodiment, a constitution other than flow channels 82*i* and 82*j* and first and second washing ports 82*a* and 82*b* of the washing instrument main body is equivalent to the above-mentioned first embodiment.

A washing instrument main body 82 of the present embodiment is a constitution in which one flow channel 82k in a joint portion 82g which becomes a supply receiving port of the washing liquid 63 branches into two flow channels 82i and 82j at different angles in the main body, to feed the liquid to each of the first and second washing ports 82a and 82b. It is to be noted that a sectional area of a diameter of the flow channel 82i is set to be larger than a sectional area of a diameter of the flow channel 82j, and an amount of the washing liquid jetting out from the first washing port 82a per hour [a first water feed amount] is set to be larger than an amount of the washing liquid jetting out from the second washing port 82b [a second water feed amount] so that a water feed force of the washing liquid 63a is larger than that of the washing liquid 63b.

In this example, the flow channel 82i extends obliquely downward from a rear side toward a front side at an acute angle (the angle from the rear side of a longitudinal axis) set to an angle $\alpha 2$. On the other hand, the flow channel 82j extends obliquely downward from the front side toward the rear side at an acute angle set to an angle $\beta 2$ (90 degrees or more). In this example, the branched flow channel 82i and flow channel 82j have an angle difference ($\beta - \alpha$). In FIG. 10, a direction in which a washing liquid 63a jets out from the first washing port 82a and a longitudinal axis direction of the flow channel 82i are present on the same axis, and a jetting angle is identical to the angle $\alpha 2$. Furthermore, a direction in which a washing liquid 63b jets out from the second washing port 82b and a longitudinal axis direction of the flow channel 82j are present on the same axis, and a jetting angle is identical to the angle $\beta 2$.

The washing liquids 63a and 63b jetting out from the first and second washing ports 82a and 82b directly collide with washing target regions of a receiving chamber 28 of the distal end constituting section 15, to perform washing. That is, the washing liquid 63a jetting out from the first washing port 82a directly sprays on a range from a front side surface and a bottom surface of the receiving chamber 28 to a back surface side of a swing base 31 to perform the washing. Furthermore, the washing liquid 63b jetting out from the second washing port 82b directly sprays on the bottom surface of the receiving chamber 28 on a rear side, a periphery of a raising shaft 32 of the swing base 31, an attaching region of a traction wire 33, and the like to perform the washing.

According to such a constitution, in a washing instrument of the present embodiment, a pressure due to a difference in water feed force between the jetting washing liquid 63a and the jetting washing liquid 63b acts in a direction to press the receiving chamber 28 of the distal end constituting section 15 onto an axial direction regulating portion 82d, thereby making it possible to hold a positioned state of the distal portion of the distal end constituting section 15. Needless to say, in accordance with the pressure required to hold this positioned state, amounts of the washing liquids jetting out from the first and second washing ports 82a and 82b (the sectional areas of the diameters) and directions in which the washing liquids 63a and 63b jet outside are suitably changed by design. It is to be noted that in the present embodiment and the fourth embodiment, there have been described examples each including two washing ports, but the number of the washing ports may be one or three or more as long as it is possible to hold the positioned state of the distal end constituting section 15 by the pressure of the water feed force and to sufficiently wash the inside of the receiving chamber.

Sixth Embodiment

Figure 11A:
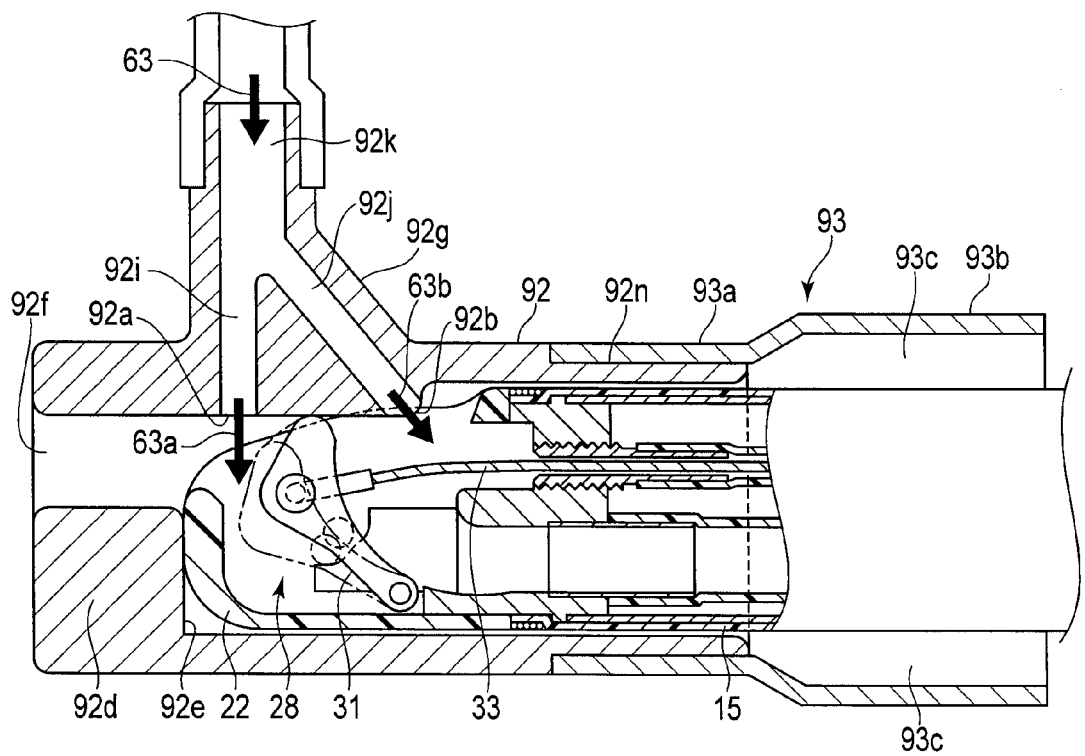
FIG. 11A is a view showing a transverse section of a washing instrument main body to which an insertion device is attached according to a sixth embodiment.
Figure 11B:
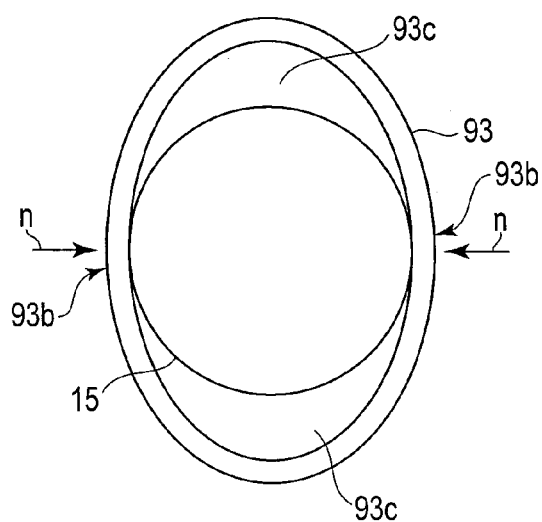
FIG. 11B is a conceptual view of the washing instrument main body seen from a rear side.

FIG. 11A is a view showing a transverse section of a washing instrument main body to which an insertion device is attached according to a sixth embodiment, and FIG. 11B is a conceptual view of the washing instrument main body seen from a rear side. The present embodiment is a constitutional example including a holding member 93 holding a positioned state of a distal end constituting section 15 of the insertion device attached to a washing instrument main body 92. In the present embodiment, a constitution other than the holding member is equivalent to the above-mentioned first embodiment.

As shown in FIG. 11A, the holding member 93 of a tubular shape which sandwiches the attached distal end constituting section 15 from both right and left sides is fitted into and attached to the rear side of the washing instrument main body 92. The holding member 93 uses an elastic member and is constituted of a cylindrical portion 93a fitted into an attaching portion 92n including a rear side stepped portion of the washing instrument main body 92, and a holding portion 93b in which an opening surface has an elliptic shape through a stepped portion tapering and extending from the cylindrical portion 93a. The holding portion 93b sandwiches the distal end constituting section 15 from both the right and left sides with an elastic force that works in an n-direction from both the sides of a narrowed side (a region of arrows 93b of FIG. 11B), and holds the distal end constituting section 15 in the positioned state of the above-mentioned embodiment. Furthermore, crescent-shaped voids 93c generated on and under the distal end constituting section 15 in the holding portion 93b of the elliptic shape shown in FIG. 11B are utilized as discharge paths of a washing liquid 63.

According to such a constitution, the distal end constituting section 15 positioned and attached to the washing instrument main body 92 is sandwiched by the holding member 93 to hold the positioned state. In this held state, the jetting washing liquid 63 directly collides with a washing target region to perform the washing. Furthermore, the washing liquid 63 after the washing passes a clearance from the washing instrument main body 92 to be discharged from the voids 93c of the holding member 93.

Furthermore, even when the distal end constituting section 15 comes out from the washing instrument main body 92 under an unintended situation, a traveling direction of jet is diffused to weaken energy of the washing liquid 63 by the washing instrument main body 92 and holding member 93, the washing liquid is discharged to the outside from an opening 92f and the voids 93c, and hence the washing liquid 63 does not spray over an operator. Furthermore, similarly to the first embodiment, the washing instrument main body 84 sinks in water to perform washing, thereby discharging the used washing liquid 63 into the water, and even when the distal end constituting section 15 comes out from the washing instrument main body 84, it is possible to prevent the used washing liquid 63 from flying and scattering to the outside.

Seventh Embodiment

Figure 13B:
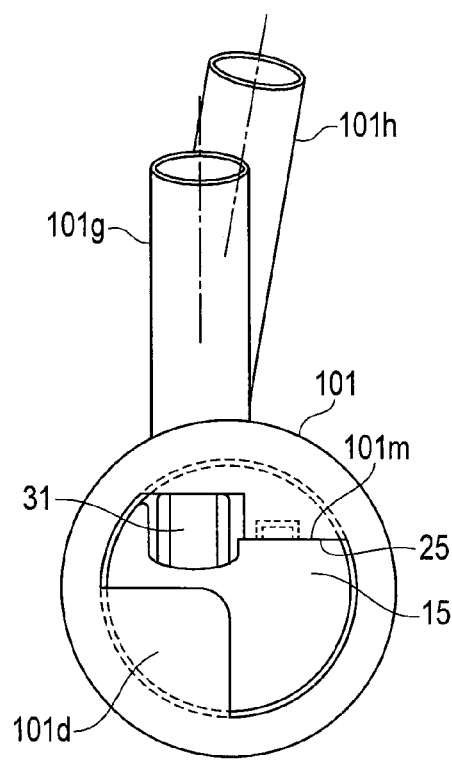
FIG. 13B is a view of the washing instrument main body to which the insertion device is attached and which is seen from a front side.
Figure 14:
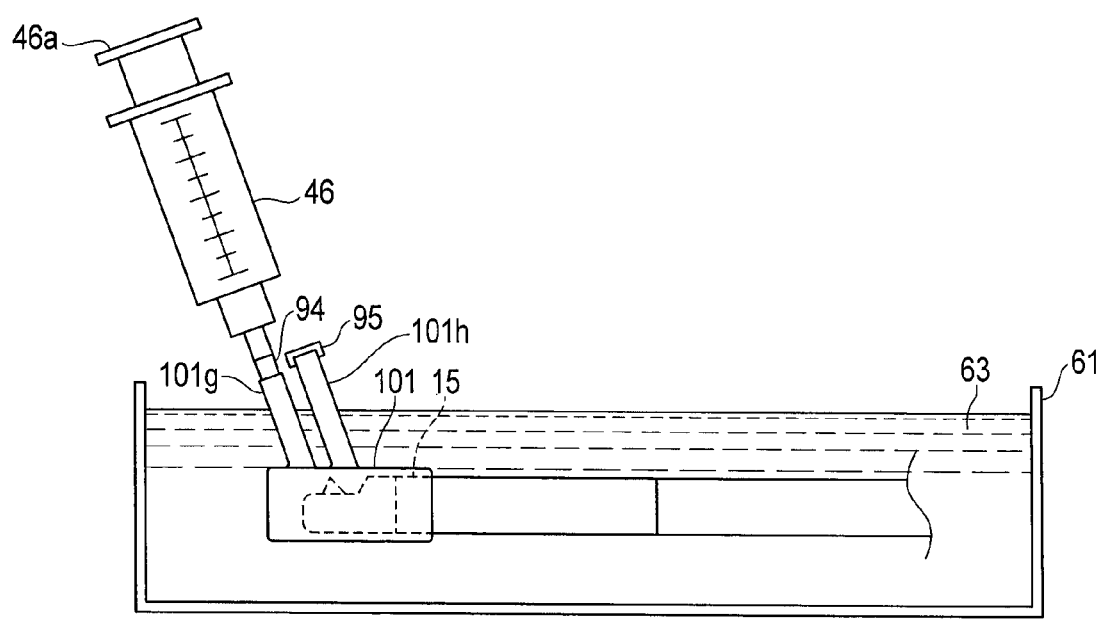
FIG. 14 is a view showing a state where the insertion device is attached to the washing instrument and washed.

FIG. 12 is a view showing an appearance constitution of a syringe for use in a washing instrument according to a seventh embodiment, FIG. 13A is a view showing a transverse section of a washing instrument main body to which an insertion device is attached, FIG. 13B is a view of the washing instrument main body to which the insertion device is attached and which is seen from a front side, and FIG. 14 is a view showing a state where the insertion device is attached to the washing instrument and washed.

The present embodiment uses a syringe 46 and a tapered nozzle 94 shown in FIG. 12 in place of the above-mentioned liquid feed mechanism constituted of the injection tube, the syringe coupling portion, the syringe and the suction tube.

The washing instrument of the present embodiment is constituted of a washing instrument main body 101 having a receiving portion forming therein a hollow of a cylindrical shape, and a liquid feed mechanism comprising the syringe 46 and the tapered nozzle 94 which supply a washing liquid 63.

The washing instrument main body 101 has joint portions 101g and 101h into which the tapered nozzle 94 is attachably/detachably inserted and which become supply receiving ports of the washing liquid 63, guide bores 101i and 101j formed in the joint portions 101g and 101h to match an outer shape of the tapered nozzle 94, and openings 101a and 101b through each of which a distal end of the tapered nozzle 94 projects from each of the guide bores 101i and 101j into the washing instrument main body 101. Furthermore, in the washing instrument main body 101, an insertion port 101c to insert a distal end constituting section 15 is provided on its rear side, an axial direction regulating portion 101d abutting on the distal end constituting section 15 is provided on its front side, and in an upper portion of an inner peripheral surface, there are provided a rotating direction regulating portion 101m facing an observation surface 25 of the distal end constituting section 15, and an opening 101f to discharge the used washing liquids 63 (63a and 63b) to the outside. The axial direction regulating portion 101d and the rotating direction regulating portion 101m constitute movement regulating portions, to position the distal end constituting section 15 at a predetermined attaching position in the washing instrument main body 101.

The joint portions 101g and 101h are set at an angle γ (an obtuse angle) to a longitudinal axis of the washing instrument main body 101 from a rear side, to pour the washing liquids 63 in parallel from an obliquely upper front to an obliquely lower rear. A swing base 31 in a receiving chamber 28 rises to bring its distal portion into contact with the inner peripheral surface of the washing instrument main body 101, and holds the positioned distal end constituting section 15.

For the opening 101a, an opening size is set so that the inserted distal end of the tapered nozzle 94 projects to a position passing a back surface side of the raised swing base 31 and reaches a position at which the washing liquid 63 directly collides with a bottom surface in the receiving chamber 28. Similarly, for the opening 101b, an opening size is set so that the inserted distal end of the tapered nozzle 94 projects to a position just before a traction wire 33 of the swing base 31 and reaches a position at which the washing liquid 63 directly collides with a periphery of a raising shaft 32 and its peripheral portion in the receiving chamber 28.

Furthermore, in the present embodiment, as shown in FIG. 13B, for the joint portion 101g, an angle of the guide bore 101i to hold the tapered nozzle 94 is set so that the washing liquid 63a can jet out vertically into the receiving chamber 28. Furthermore, in the joint portion 101h for the washing liquid 63 into the receiving chamber 28, an angle of the guide bore 101j to hold the tapered nozzle 94 is set to a vertically inclined angle so that the jetting washing liquid 63 turns in the receiving chamber.

Washing of the insertion device by the washing instrument will be described with reference to FIG. 14.

The distal end constituting section 15 is positioned and attached to the washing instrument main body 101, and the washing instrument main body is disposed in a drain tray 61. At this time, when a liquid such as water is beforehand put in the drain tray 61 and the washing instrument main body 101 is sunk, energy of the washing liquid 63 discharged from the washing instrument main body 101 weakens, thereby making it possible to prevent the washing liquid from flying and scattering around the drain tray 61.

Next, the distal end of the tapered nozzle 94 is placed in the washing liquid 63 stored in a container, and a plunger 46a is pulled to suck the washing liquid 63, thereby storing the liquid in the syringe 46. The tapered nozzle 94 is inserted from an opening of the guide bore 101i of the joint portion 101g until abutting and is attached. At this time, the joint portion 101h is hermetically sealed with a leak preventing cap 95 to tightly close an opening of the other guide bore 101j. This hermetic seal is used to prevent the washing liquid 63 from flowing backward to the guide bore 101j and leaking out from the joint portion 101h, when the washing liquid is poured from the joint portion 101g.

Next, the plunger 46a is pushed into the syringe 46, and the received washing liquid 63 jets out from the distal end of the tapered nozzle 94 into the receiving chamber 28 with great energy. The jetting washing liquid 63a directly collides with the back surface side of the swing base 31 in the receiving chamber 28 and the bottom surface of the receiving chamber 28 to perform washing. At this time, the washing liquid 63a turns to a front side (a raised upper surface side) of the swing base 31, the periphery of the raising shaft 32, an attaching region of the traction wire 33 or the like to perform the washing. The washing liquid 63a after the washing flows out from the opening 101f and a clearance between the distal end constituting section 15 and the washing instrument main body 101, and is discharged into the drain tray 61. It is to be noted that when flowing out from the clearance, the washing liquid 63a is discharged to the drain tray 61 while washing a peripheral portion of the distal end constituting section 15.

Next, the syringe 46 is extracted from the joint portion 101g, and the leak preventing cap 95 is moved from the joint portion 101h to the joint portion 101g to perform the hermetic sealing. The new washing liquid 63 is sucked and received in the syringe 46, and then the tapered nozzle 94 is inserted into the joint portion 101h. Subsequently, the plunger 46a is pushed into the syringe 46, and the washing liquid 63b jets out from the distal end of the tapered nozzle 94 into the receiving chamber 28 with great energy.

The jetting washing liquid 63b directly collides with the front side (the raised surface side) of the swing base 31 in the receiving chamber 28, the periphery of the raising shaft 32, the attaching region of the traction wire 33 or the like to perform the washing. Furthermore, at this time, the washing liquid 63b turns to the back surface side of the swing base 31 to perform the washing. The washing liquid 63b after the washing flows out from the opening 101f and the clearance and is discharged into the drain tray 61 in the same manner as in the washing liquid 63a. It is to be noted that when flowing out from the clearance, the washing liquid 63b is discharged to the drain tray 61 while washing the peripheral portion of the distal end constituting section 15.

It is to be noted that a space between the joint portion 101g and the joint portion 101h is formed as a space via which two syringes are simultaneously attached, and the two syringes are attached, so that it is also possible to alternately or simultaneously push the plungers, thereby performing the washing. However, in the case of simultaneously pushing the plungers, two operators push the plungers when the two plungers are not present in a range that is reachable with one hand or when the syringe 46 is not fixed to the drain tray 61.

According to such a constitution, the distal end of the attached tapered nozzle 94 easily reaches the region just before the washing target region, and hence with the washing liquids 63a and 63b jetting out from the tapered nozzle 94, it is possible to strongly wash the back side of the swing base 31, the periphery of the raising shaft 32, the attaching region of the traction wire 33, or the like. Furthermore, the washing instrument is only constituted of the washing instrument main body 101 and the syringe 46, and can be achieved at low cost.

Eighth Embodiment

FIG. 15A is a view showing an appearance constitution of a syringe for use in a washing instrument according to an eighth embodiment, and FIG. 15B is a view showing a transverse section of a washing instrument main body to which the syringe is attached.

The present embodiment is an example in which the present embodiment is only constituted of a syringe, but in the above-mentioned seventh embodiment, a liquid feed mechanism of a washing liquid is constituted of a combination of the syringe 46 and the tapered nozzle 94.

A syringe 102 shown in FIG. 15A is constituted of a plunger 102a, and a tube main body (an injection tube) to which a comparatively short tapered distal portion 102b is integrally attached. A washing instrument main body 103 is a constitution equivalent to the washing instrument main body 101 in the above-mentioned seventh embodiment, and guide bores 103i and 103j of joint portions 103g and 103h are formed to match an outer shape of the distal portion 102b of the syringe 46.

According to such a constitution, it is possible to produce an effect equivalent to that of the above-mentioned seventh embodiment, and further the number of components decreases, cost accordingly decreases, and management of the constituent components becomes easy.

According to the embodiments of the present invention, it is possible to provide a washing instrument for an insertion device which holds the insertion device attached to a predetermined position of a washing instrument main body and in which washing liquids directly jet out to washing target regions from different directions to perform washing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A washing instrument for an insertion device, the insertion device comprising a distal end constituting section configured to accommodate a swing base and a drive mechanism, the drive mechanism configured to raise and invert the swing base, the distal end constituting section comprising a side surface with an aperture, the washing instrument comprising:
    a washing instrument main body having a tubular hollow receiving portion that is configured to receive the distal end constituting section;
    a liquid feed mechanism that is configured to feed a washing fluid from an outside into the receiving portion;
    washing ports which are provided away from one another in an inner peripheral surface of the receiving portion and from which the fluid fed from the liquid feed mechanism is configured to jet out in directions which intersect a longitudinal axis direction of the receiving portion and which are different from one another; and
    a movement regulating portion that is configured to position the distal end constituting section at a position at which the fluid jetting out from the washing ports directly collides with respective desirable washing targets in the aperture of the distal end constituting section received in the receiving portion,
    wherein, responsive to raising of the swing base, the inner peripheral surface of the receiving portion is configured to be pressed by a distal portion of the swing base, lock the distal end constituting section and maintain a positioned state of the distal end constituting section.

2. The washing instrument for the insertion device according to claim 1,
    wherein the movement regulating portion includes:
    a first movement regulating portion configured to contact a front surface of the distal end constituting section and inhibit the insertion device from moving in the longitudinal axis direction of the receiving portion; and
    a second movement regulating portion configured to contact a flat surface in a portion of an outer periphery of the distal end constituting section and inhibit the insertion device from rotating about a longitudinal axis of the receiving portion.

3. The washing instrument for the insertion device according to claim 1,
    wherein the inner peripheral surface of the receiving portion comprises a convex locking portion at a position configured to be pressed by the distal portion of the swing based when raised, the locking portion configured to engage with the distal portion of the swing base.

4. The washing instrument for the insertion device according to claim 3, wherein the locking portion, comprises one corner configured to engage with the aperture of the distal end constituting section, and another corner is configured to engage with the distal portion of the swing base when raised, so that the positioned state of the distal end constituting section is maintained.

5. The washing instrument for the insertion device according to claim 1, wherein the washing ports are arranged so that the swing base is positioned between two washing ports in the longitudinal axis direction of the receiving portion.

6. The washing instrument for the insertion device according to claim 1, wherein the movement regulating portion positions the distal end constituting section at a position at which the fluid jetting out from the washing ports in different directions directly collides with a desirable washing target in the aperture.

7. The washing instrument for the insertion device according to claim 1,
    wherein the distal end constituting section comprises a chamber configured to accommodate the swing base and the drive mechanism, the chamber comprising a side surface with an aperture,
    the washing ports are configured to jet out the liquid into the chamber through the aperture of the distal end constituting section, and
    the movement regulating portion is configured to position the distal end constituting section at a position at which the fluid jetting out from the washing ports directly collides with a washing target in the chamber.

8. A washing instrument for an insertion device, the insertion device comprising a distal end constituting section configured to accommodate a swing base and a drive mechanism, the drive mechanism configured to raise and invert the swing base, the distal end constituting section comprising a side surface with an aperture, the washing instrument comprising:
- a washing instrument main body having a tubular hollow receiving portion that is configured to receive the distal end constituting section;
- a liquid feed mechanism that is configured to feed a washing fluid from an outside into the receiving portion;
- washing ports which are provided away from one another in an inner peripheral surface of the receiving portion and from which the fluid fed from the liquid feed mechanism that is configured to jet out in directions which intersect a longitudinal axis direction of the receiving portion and which are different from one another; and
- a movement regulating portion that is configured to position the distal end constituting section at a position at which the fluid jetting out from the washing ports directly collides with respective desirable washing targets in the aperture of the distal end constituting section received in the receiving portion,
- wherein the inner peripheral surface of the receiving portion is configured to lock the distal end constituting section and maintain a positioned state of the distal end constituting section by allowing the fluid jetting out from at least one of the washing ports into the aperture to collide in a direction to press the insertion device onto the movement regulating portion.

9. The washing instrument for the insertion device according to claim 8,
wherein the washing ports include:
- a first washing port that is configured to supply the fluid in the direction to press the insertion device onto the movement regulating portion; and
- a second washing port that is configured to supply the fluid to a side different from the direction to press the insertion device onto the movement regulating portion, and
- a pressure due to a difference in water feed force between the fluid jetting out from the first washing port and the fluid jetting out from the second washing port is configured to maintain the positioned state of the distal end constituting section.

10. The washing instrument for the insertion device according to claim 8,
wherein the aperture of the distal end constituting section is configured to open in a direction crossing a longitudinal axis direction of the washing instrument main body, and
the swing base and the drive mechanism are arranged in the aperture to change a traveling direction of a treatment instrument extending out from the aperture.

11. The washing instrument for the insertion device according to claim 10, wherein the washing ports are arranged so that the swing base is positioned between two washing ports in the longitudinal axis direction of the receiving portion.

12. The washing instrument for the insertion device according to claim 8, wherein the movement regulating portion is configured to position the distal end constituting section at a position at which the fluid jetting out from the washing ports in different directions directly collides with a desirable washing target in the aperture.

13. The washing instrument for the insertion device according to claim 8,
wherein the distal end constituting section comprises a chamber that is configured to accommodate the swing base and the drive mechanism, the chamber comprising a side surface with an aperture,
the washing ports are configured to jet out the liquid into the chamber through the aperture of the distal end constituting section, and
the movement regulating portion is configured to position the distal end constituting section at a position at which the fluid jetting out from the washing ports directly collides with a washing target in the chamber.

* * * * *